United States Patent [19]

Perez et al.

[11] Patent Number: 5,019,068

[45] Date of Patent: May 28, 1991

[54] WASHABLE DIAPER WITH ABSORBENT LINER

[75] Inventors: Sam S. Perez; Susan Malinowski, both of Grimsby, Canada

[73] Assignee: Diana Dolls Fashions, Inc., Stoney Creek, Canada

[21] Appl. No.: 474,946

[22] Filed: Feb. 5, 1990

[51] Int. Cl.⁵ .............................................. A61F 13/00
[52] U.S. Cl. .................................. 604/386; 604/393; 604/395; 604/401
[58] Field of Search ............... 604/378, 396, 401, 399, 604/385.1, 358, 364, 395

[56] References Cited

U.S. PATENT DOCUMENTS

| 2,545,761 | 3/1951 | Brink | 604/401 |
| 2,636,494 | 4/1953 | Hon | 604/396 |
| 3,050,063 | 8/1962 | Margraf | 604/401 |
| 3,162,196 | 12/1964 | Salk | 604/401 |
| 3,247,846 | 4/1966 | Fansler | 604/401 |
| 3,395,708 | 8/1968 | Hervey et al. | 604/399 |
| 4,615,695 | 10/1986 | Cooper | 604/394 |
| 4,623,341 | 11/1986 | Roeder | 604/378 |
| 4,747,846 | 5/1988 | Boland et al. | 604/396 |
| 4,801,298 | 1/1989 | Sorenson et al. | 604/378 |
| 4,838,886 | 6/1989 | Kent | 604/396 |

Primary Examiner—Stephen C. Pellegrino
Assistant Examiner—Gary Jackson
Attorney, Agent, or Firm—Smart & Biggar

[57] ABSTRACT

An improved washable diaper is provided with an absorbent liner that is folded within the diaper during use for improved absorbency and, following use, extends from the diaper for improved efficiency of cleaning and drying. An additional liner may be secured to the liner in cases where extra absorbency is required, such as for overnight use, and removed from the liner for cleaning and drying. The liners provide additonal layers of absorbent cloth while their separation from the diaper body following use avoids the difficulties of cleaning and drying presented by a number of cloth layers permanently secured to one another.

10 Claims, 4 Drawing Sheets

WASHABLE DIAPER WITH ABSORBENT LINER

FIELD OF THE INVENTION

This invention relates to a washable diaper and, in particular, a washable diaper that is provided with one or more additional absorbency liners that may be fully or partially separated from the main body portion of the diaper to facilitate cleaning and drying.

BACKGROUND OF THE INVENTION

Washable diapers have long been known and have, in the past, taken many forms. Such diapers have commonly been constructed of various cloth fabrics and have comprised a number of layers of such fabric to provide adequate absorption. The layers of previous washable diapers have been formed either through folding one large piece of fabric over upon itself in unsecured relationship or through permanently securing a number of smaller fabric pieces to one another.

The disadvantage of a washable diaper that is formed of a number of cloth layers is that when those layers are secured to one another, the drying process following washing becomes very time consuming. The previous use of one large piece of fabric which could be folded for use as a diaper and unfolded for cleaning avoided the difficulty of extended time for drying but resulted in a diaper that was poorly fitted, particularly in the area of the legs, thus leading to discomfort to the wearer and frequent moisture leakage. An additional waterproof pant with gathered leg portions has often been required to cover the folded diaper in order to avoid the leakage problem.

We have found that we can provide a washable diaper that has improved absorbency, is contoured to fit the wearer appropriately and also in which the layers are, to a degree, separable to allow for more efficient cleaning and drying. A liner that is partially attached to the diaper may be folded within the diaper during use for extra absorbency. Because the liner is only partially attached to the diaper, air can circulate freely between the liner and the diaper during drying. An additional secondary liner may also be attached to the liner for increased absorbency and fully detached from the liner for cleaning and drying.

SUMMARY OF THE INVENTION

According to one aspect of the present invention, there is provided a washable cloth diaper of the type which has front and back waist band portions between which a multiplicity of layers of cloth extend in an intimate overlying relationship to form a highly absorbent main body portion, the improvement of, an absorbent primary liner which has a first edge secured to one of said waistband portions, said primary liner having a body portion extending from said first edge which has a sufficient length to extend from the waistband portion to which it is attached to overlap a portion of said main body to cooperate therewith to increase the absorption capacity of the diaper in use, said body portion being free of attachment to the main body portion of the diaper whereby the body of the liner may be spaced from the main body of the diaper to facilitate drying of the diaper.

According to another aspect of the present invention, there is provided a washable diaper comprising a highly absorbent main body portion comprising a multiplicity of layers secured to one another in overlying relationship and having oppositely disposed side edges which are contoured and gathered to provide leg-conforming fit in use and front and back waist portions; and, a highly absorbent primary liner comprising at least two layers secured to one another in overlying relationship, said primary liner being hingedly attached to one of said waist portions for movement between a first position overlying at least a portion of the main body portion to increase the absorption capacity of the diaper and a second position in which the primary liner is spaced from the main body portion to permit substantial exposure of the primary liner and main body portion during drying of the diaper after washing.

BRIEF DESCRIPTION OF THE DRAWINGS

In drawings which illustrate embodiments of the invention.

DESCRIPTION OF THE PREFERRED EMBODIMENT

Figure 1:
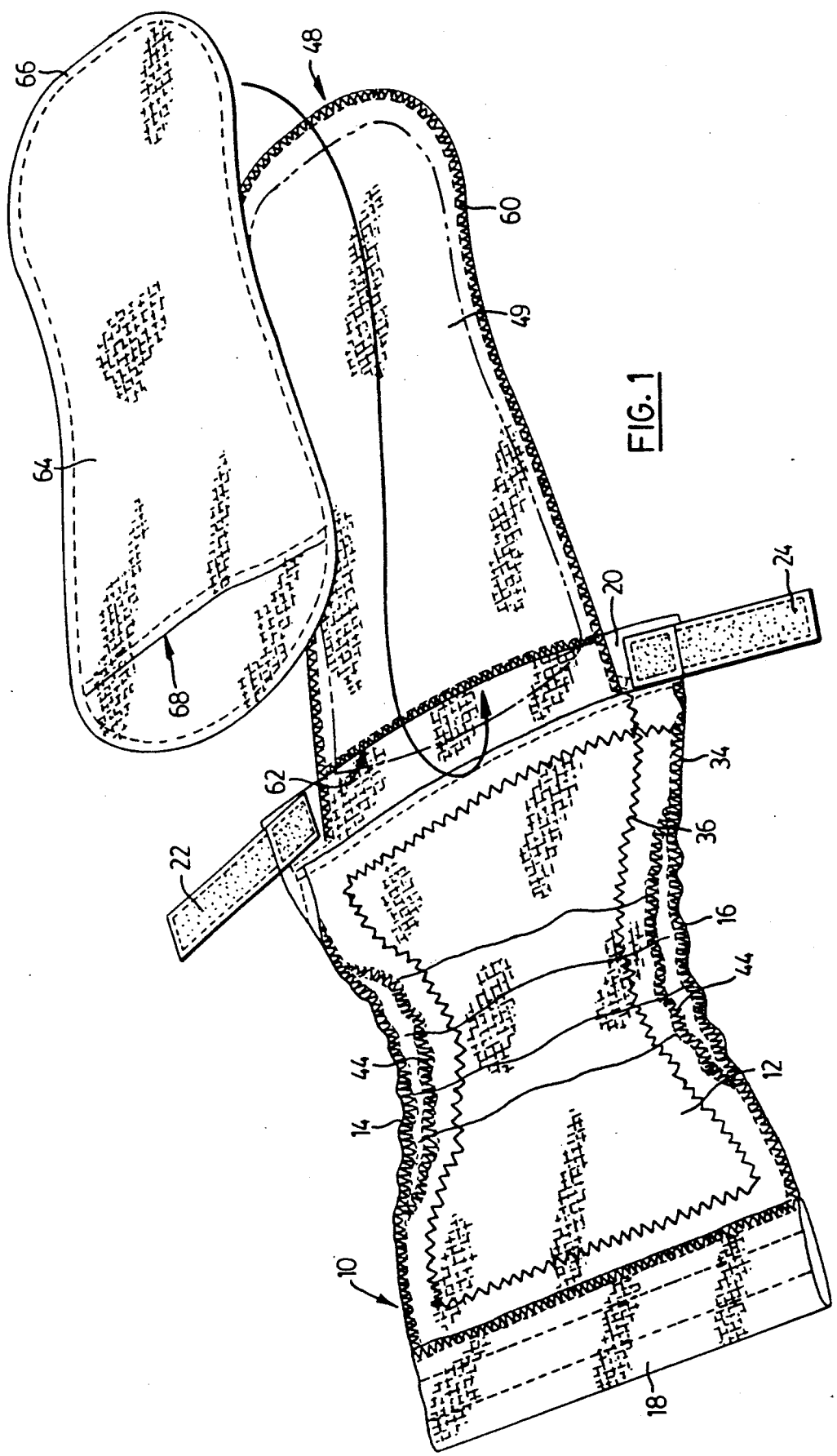
FIG. 1 is a top perspective view of the diaper with primary and secondary liners.

With reference to FIG. 1 of the drawings, reference numeral 10 refers to the washable cloth diaper. The main body portion 12 has side edges 14 and 16 which are contoured and gathered to fit snugly around the wearer's legs. The front of the diaper 10 is provided with waistband 18. The back of the diaper 10 is also provided with a back waistband 20 and, additionally with tabs 22 and 24 that may be secured to the front waistband 18 with VELCRO TM or a like fastening means. When the diaper 10 is in place on the wearer and the tabs 22 and 24 are secured to the front waistband 18, the front waistband 18 and back waistband 20 form a continuous circle around the waist of the wearer.

Figure 3:
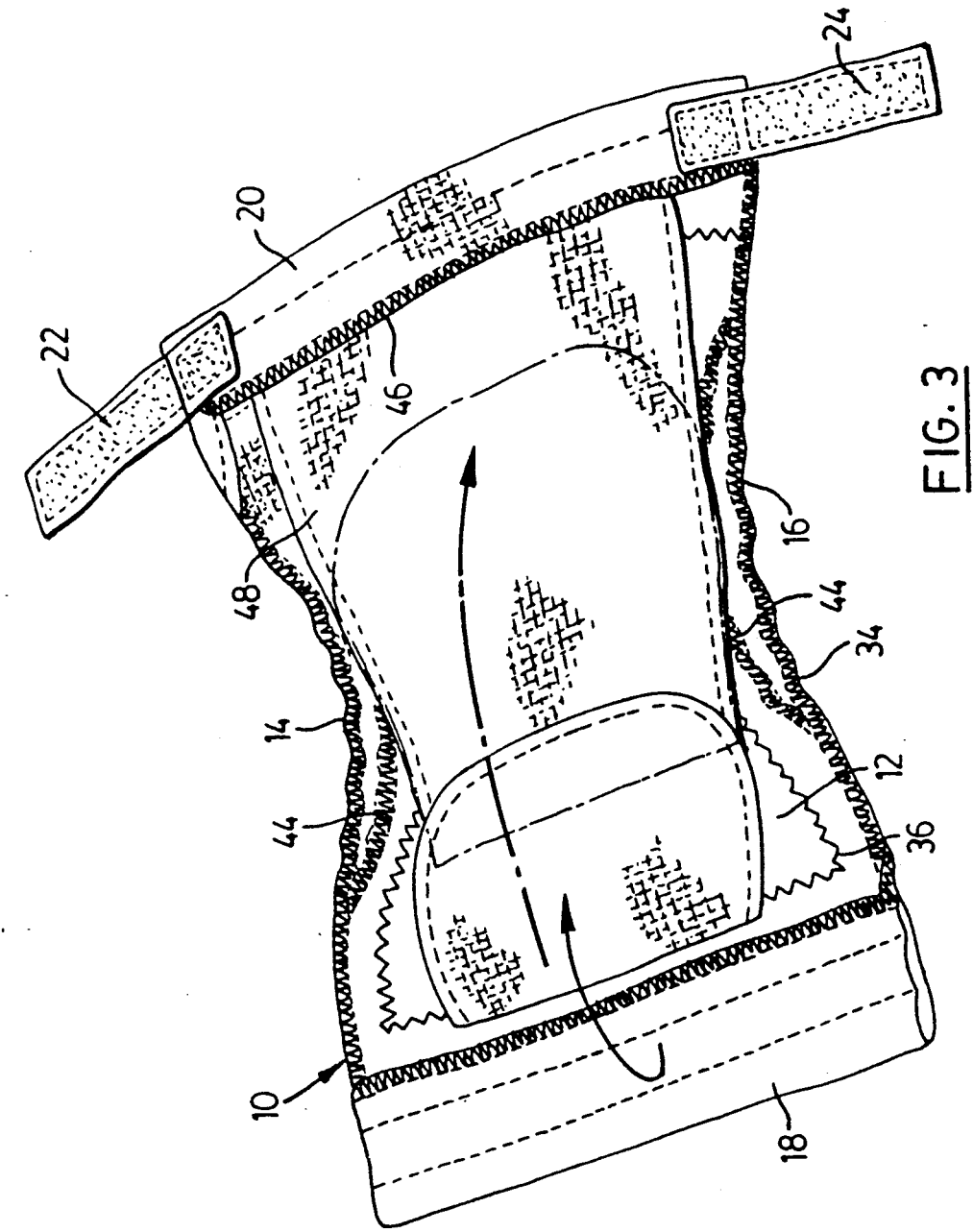
FIG. 3 is a top perspective view showing the primary liner folded with the main body portion of the diaper; and, FIG. 4 is a view showing the various layers of the diaper and liner.
Figure 4:
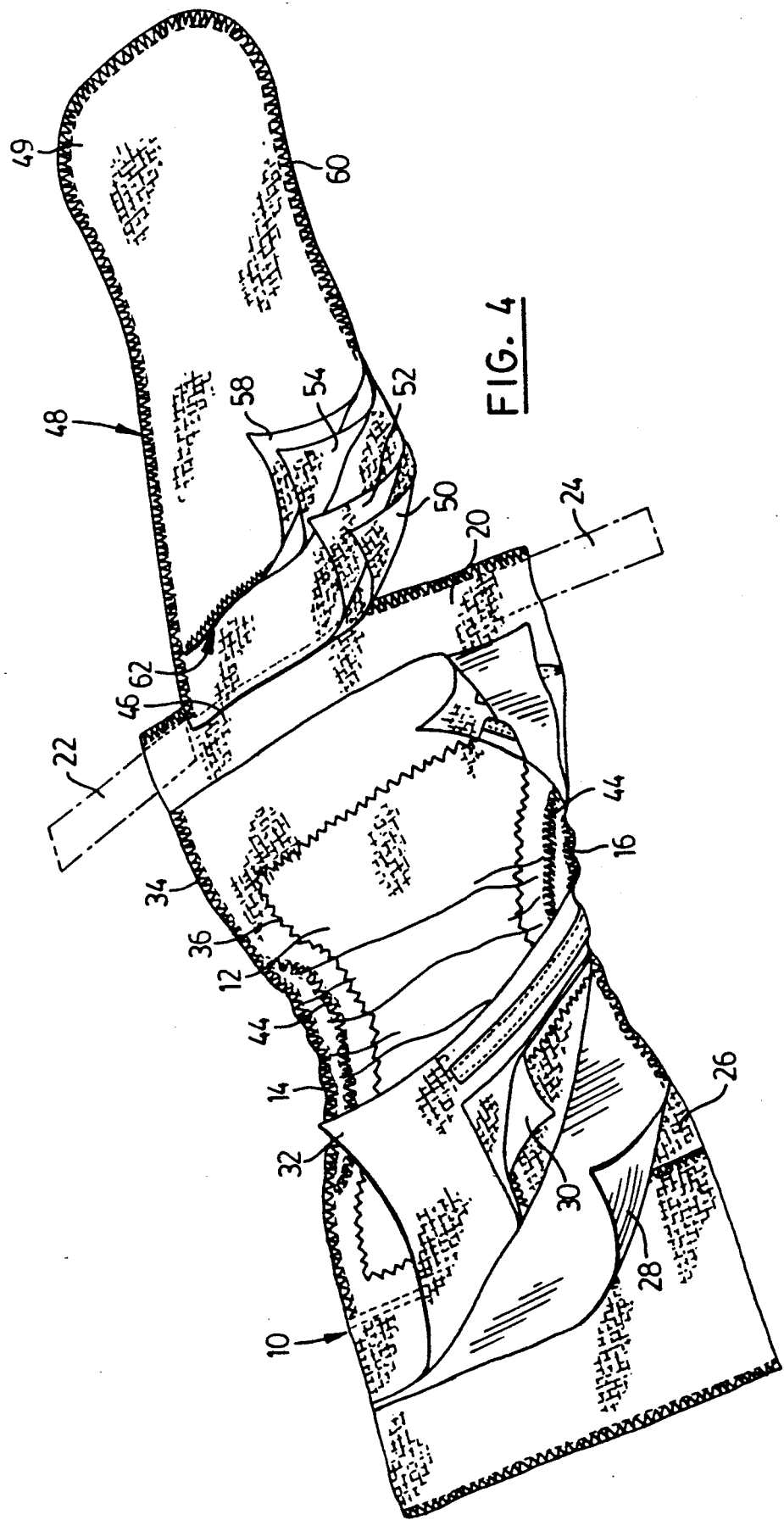

As is shown in FIG. 4, the main body portion 12 of the diaper 10 comprises a number of layers including an outer sheet 26, a plurality of intermediate sheets 28 and 30 and an inner sheet 32. Preferably, the outer of the intermediate sheets 28 and 30 is of a liquid impermeable material to minimize leakage. The various layers of the main body portion 12 are permanently secured to one another in overlying relationship by stitching along stitch lines 34 and 36 which completely closes the layers of the main body portion in the manner shown in FIGS. 1, 2 and 3. Additional stitching 44 is gathered and elasticized at the side edges 14 and 16.

A primary liner 48 is fastened to the main body portion 12 of the diaper 10 in the area of the back waistband 20 along edge 46 but is otherwise free of attachment to the main body portion 12 so that the body portion 49 of the primary liner 48 is free to extend in a spaced relationship with respect to the main body portion 12. In FIG. 1 the primary liner 48 is shown extending away from the main body portion 12 and in FIG. 2 the primary liner is shown lying across the main body portion 12.

As is shown in FIG. 4, the primary liner 48 comprises a number of layers including outer sheets 50 and 58 and a plurality of intermediate sheets 52 and 54. The sheets 50, 52, 54 and 58 lie in overlapping relationship and are permanently secured to one another by stitching 60 around the periphery of the sheets 50,52, 54 and 58. However, two of the intermediate layers 52 and 54 remain unsecured along one seam to provide opening 62.

In cases where additional absorbency is required a secondary liner 64, shown in FIG. 1, is inserted into the opening 62 in the primary liner 48 to lie in overlapping relationship with the layers of the primary liner 48. The secondary liner 64 also comprises a plurality of absorbent layers lying in overlapping relationship and secured to one another by stitching 66 around the periphery of the liner 64. Similarly to the primary liner 48, two layers of the secondary liner 64 remain unattached to one another along one seam to provide an opening 68.

Figure 2:
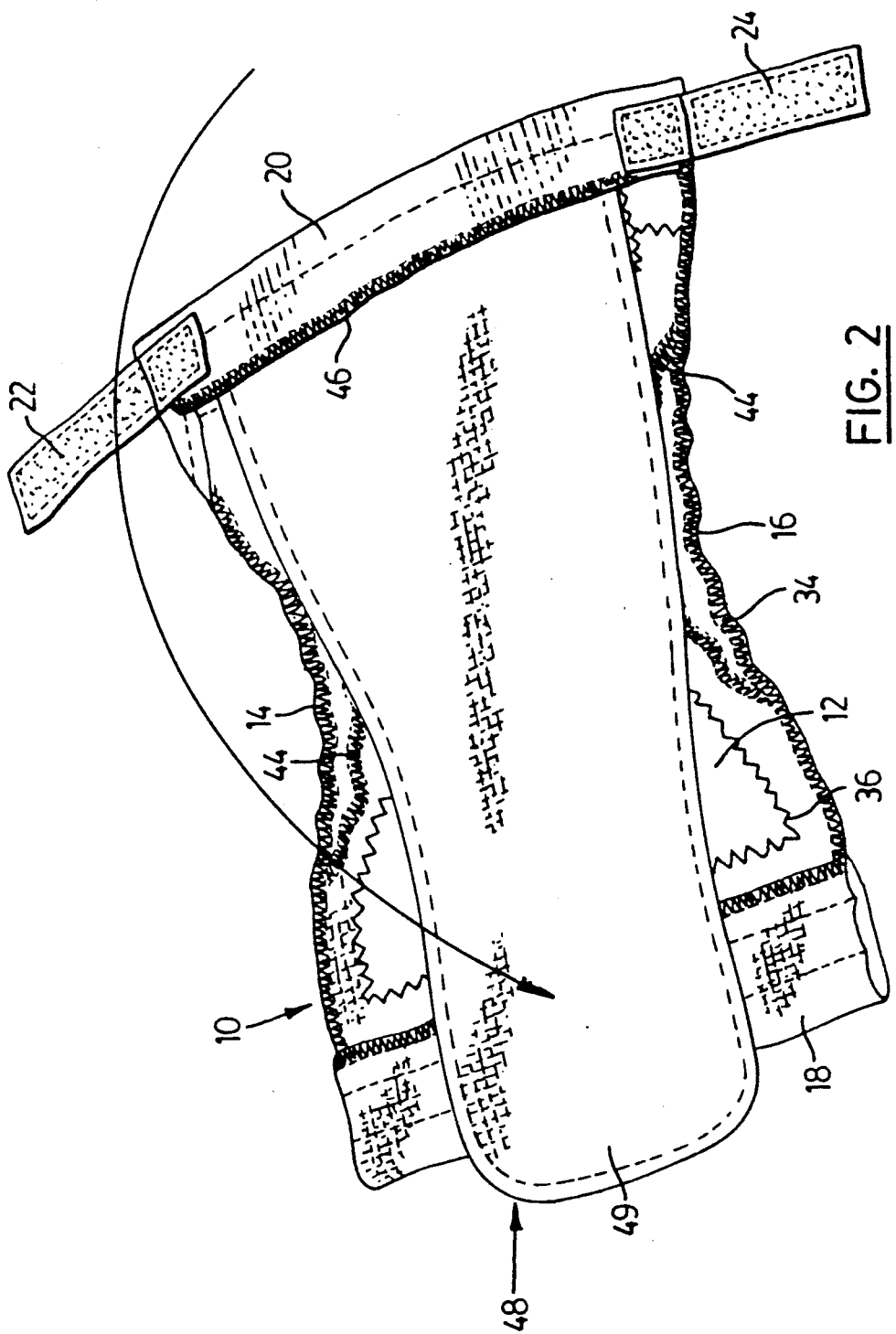
FIG. 2 is a view similar to FIG. 1 showing the primary liner placed across the main body portion of the diaper.

In use, the main body portion 12 of the diaper 10 is extended flat and the primary liner 48 is placed across the diaper 10 as is illustrated in FIG. 2. From this position, the primary liner 48 can be folded as illustrated in FIG. 3, to lie within the confines of the main body portion 12. The folds create extra moisture absorbing layers and their placement can be varied to provide the greatest bulk of liner 48 toward the front or back of the main body portion 12 of the diaper 10, as appropriate depending on whether the user is male or female. In FIG. 3, the solid arrow indicates a forwardly positioned fold while the broken arrow indicates a rearward positioning of the fold. The main body portion 12 is then fitted to the wearer and the front 16 and back 18 waistbands are secured together through the attachment of tabs 20 and 22, so that the front and back waistbands encircle the wearer's waist.

After the diaper 10 has been soiled, it can be washed and dried using conventional washing and drying machines. Because the major portion of the primary liner 48 is not attached to the main body 12, the tumbling action of the washing machine or a dryer will tend to cause relative movement to occur between the primary liner 48 and the main body of the diaper 12 and as a result, some separation will occur between the primary liner 48 and the main body 12. This separation will serve to expose the surface of the primary line 48 to the cleaning fluids or drying air thus leading to improved cleaning and a reduction in the time period required for drying.

In cases where additional absorption is necessary, such as overnight use of the diaper, the secondary liner 64 may be inserted into the opening 62 in the primary liner 48 to lie in overlapping relationship with the various sheets 50, 52, 54 and 58 of the primary liner 48. Thus, the primary liner 48 is provided with additional absorption layers. After use, the secondary liner 64 can be removed from the primary liner 48 and washed and dried unattached to the main body portion of the diaper or primary liner 48. The separate nature of the secondary liner 64 allows it to be used as an optional feature only in situations where it is required and allows for more efficient cleaning and drying than the additional of more permanently secured layers to the main body portion 12 or the primary liner 48. The opening 68 in the secondary liner 64 also aids in the drying process by allowing the circulation of air between layers.

I claim:

1. In a washable cloth diaper of the type which has front and back waist band portions between which a multiplicity of layers of cloth extend in an intimate overlying relationship to form a highly absorbent main body portion, the improvement of, an absorbent primary liner which has a first edge secured to one of said waistband portions, said primary liner having a body portion extending from said first edge which has a sufficient length to extend from the waistband portion to which it is attached to overlap a portion of said main body to cooperate therewith to increase the absorption capacity of the diaper in use, said body portion being free of attachment to the main body portion of the diaper whereby the body of the liner may be spaced from the main body of the diaper to facilitate drying of the diaper.

2. A diaper as claimed in claim 1 having a secondary liner comprising at least two layers secured to one another in overlying relationship that may be secured to the primary liner for additional absorbency during use and removed from the primary liner following use to facilitate drying of the diaper.

3. A diaper as claimed in claim 1 wherein the primary liner is attached to the front waistband portion.

4. A washable diaper comprising:
   (a) a highly absorbent main body portion comprising a multiplicity of layers secured to one another in overlying relationship and having oppositely disposed side edges which are contoured and gathered to provide leg-conforming fit in use and front and back waist portions;
   (b) a highly absorbent primary liner comprising at least two layers secured to one another in overlying relationship, said primary liner being hingedly attached to one of said waist portions for movement between a first position overlying at least a portion of the main body portion to increase the absorption capacity of the diaper and a second position in which the primary liner is spaced from the main body portion to permit substantial exposure of the primary liner and main body portion during drying of the diaper after washing.

5. A diaper as claimed in claim 4 having a secondary liner comprising at least two layers secured to one another in overlying relationship that may be secured to the primary liner for additional absorbency during use and removed from the primary liner following use for ease of cleaning.

6. A diaper as claimed in claim 5 wherein the secondary liner is proportioned to fit within the primary liner and the primary liner is provided with an opening into which the secondary liner may be inserted for use.

7. A diaper as claimed in claims 4, 5 or 6 wherein the primary liner comprises an elongate tube constructed of absorbent fabric, the tube being of a length that is greater than the length of the main body portion and in use, arranged in overlapping folds within the main body portion for additional absorbency.

8. A diaper as claimed in claim 7 wherein the layers of the secondary liner are unsecured to one another along one edge thereof, thus providing an opening to allow air to circulate between layers to facilitate drying of the liner following cleaning.

9. A diaper as claimed in claims 5 or 6 wherein the layers of secondary liner are unsecured to one another along one edge thereof thus providing an opening to allow air to circulate between layers to facilitate drying of the liner following cleaning.

10. A diaper as claimed in claims 4 or 6 wherein at least one of the layers of the main body portion is of a moisture impermeable material which forms a moisture barrier which prevents leakage through the main body portion.

* * * * *